United States Patent [19]

France, Jr.

[11] Patent Number: 4,906,186
[45] Date of Patent: Mar. 6, 1990

[54] TEMPLATE FOR SETTING ARTIFICIAL TEETH IN A DENTURE

[76] Inventor: Stanley L. France, Jr., 3427 Crestview Ct., Napa, Calif. 94558

[21] Appl. No.: 264,842

[22] Filed: Oct. 31, 1988

[51] Int. Cl.$^4$ .............................................. A61C 19/04
[52] U.S. Cl. ....................................... 433/72; 433/196
[58] Field of Search .................... 433/68, 72, 73, 196, 433/213

[56] References Cited

U.S. PATENT DOCUMENTS

| | | | |
|---|---|---|---|
| 1,589,973 | 6/1926 | Landa | 433/72 |
| 3,508,333 | 4/1970 | Guichet | 433/73 |
| 3,579,832 | 5/1971 | Cooper, Jr. | 433/72 |
| 4,059,899 | 11/1977 | Dyal | 433/72 |
| 4,265,619 | 5/1981 | Lucki et al. | 433/213 |

Primary Examiner—John J. Wilson
Assistant Examiner—Adriene J. Lepiane
Attorney, Agent, or Firm—Melvin R. Stidham

[57] ABSTRACT

A template for setting artificial teeth comprises a pair of arched ridge formers pivoted at their front ends to a base so that the overall arch may be made wider or narrower to coincide with the curve of a model of the patient's opposing jaw. Shallow receptacles in the surfaces of the pivoted ridge formers receive the individual artificial teeth so they can be waxed to a base plate made from an impression of the patient's jaw.

6 Claims, 2 Drawing Sheets

TEMPLATE FOR SETTING ARTIFICIAL TEETH IN A DENTURE

BACKGROUND OF THE INVENTION

It requires years of training and experience to develop the skills needed to set artificial teeth in a denture. The dental technician sets each tooth individually in a wax rim on an acrylic base plate, which is made from a model of the patient's jaw, the model having been cast from a negative impression of the patient's jaw made by the dentist. In setting the artificial teeth, each tooth must be at a particular angle of inclination and with the biting or grinding surfaces following the "Curve of Spee" wherein the protrusion of the teeth from the gums is reduced gradually from front to rear. The painstaking work is generally done by visual assessment, without templates or patterns.

OBJECTS OF THE INVENTION

It is an object of this invention to provide a template for setting artificial teeth enabling one to position teeth on a base plate to form a denture with a desired bite pattern.

It is a further object of this invention to provide a template enabling one to set artificial teeth in a denture at proper angles and along a desired curvature.

It is a further object of this invention to provide a template for setting artificial teeth that is adjustable in accordance with the size and curvature of the patient's jaw.

Other objects and advantages of this invention will become apparent from the description to follow, particularly when read in conjunction with the accompanying drawings.

SUMMARY OF THE INVENTION

In carrying out this invention, I provide a template comprising a base on which are pivotally mounted two arched segments, each representing one-half of a patient's jaw from front to rear. When the segments are pivoted to form the proper full arch corresponding to that of the patient's opposing jaw, a plurality of shallow receptacles in the segments are disposed along the arch in which they are to be set. The teeth are caused to stand up in the receptacles so that they are disposed at the proper angles of inclination to then be waxed into a base plate made from a model of the patient's jaw.

DESCRIPTION OF A PREFERRED EMBODIMENT

Figure 1:
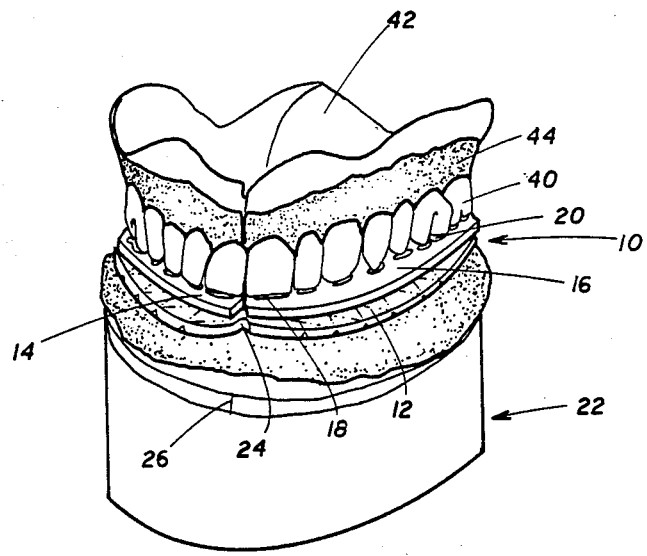
FIG. 1 is a view in perspective of the template for setting artificial teeth and a denture formed therewith.
Figure 2:
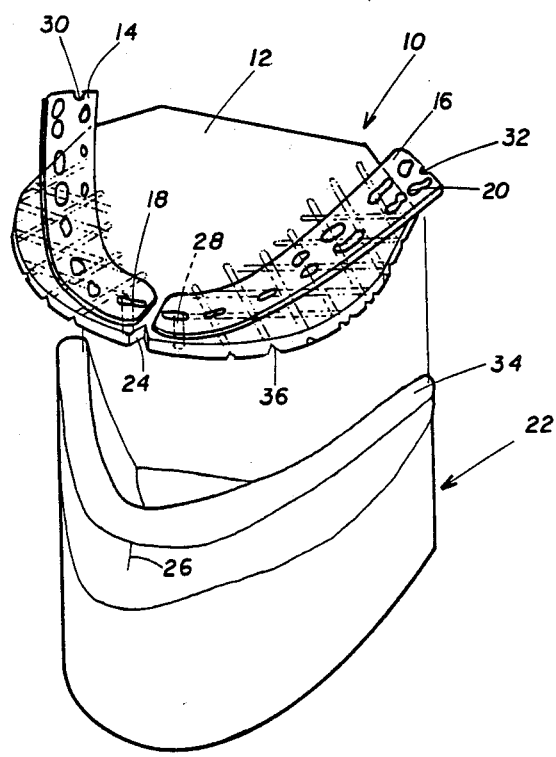
FIG. 2 is a view in perspective of the template being positioned on a model of the patient's opposing jaw.

Referring now to the drawings with greater particularity, the template of this invention 10 for setting artificial teeth comprises a base member 12 of any suitable material, such as a plastic on which are pivotally mounted arched ridge formers 14 and 16 with shallow receptacles or indentations 18 and 20 positioned to represent impressions that would be made by teeth if they were ideally arranged in the human jaw. While the template 10 may be configured to prepare dentures for the upper or lower jaw, it is preferably used in the preparation of the upper denture.

Assuming that the template 10 is to be used for the preparation of the upper denture, it is positioned precisely on a model 22 of the patient's lower jaw, which is cast from an impression made by the dentist. In positioning the template 10, a centering notch 24 in the template base member is aligned with a midpoint marker made in the lower jaw model 22. The arched ridge formers 14 and 16 are then pivoted about pins 28 until the front indentations 18, as well as ridge notches 30 and 32 are disposed along the center of the ridge 34 of the lower jaw model 22.

During preparation of the denture, the template 10 is held in place by gripping a soft clay or the like on the lower jaw ridge 34, with cleats or grooves 36 in the bottom of the base member 12. Then, when the pivoted ridge formers 14 and 16 are pivoted to their desired positions, as indicated by the arrows in FIG. 3, they may be held in place on the base member 12 by suitable material, such as melted wax.

Figures 3, 4:
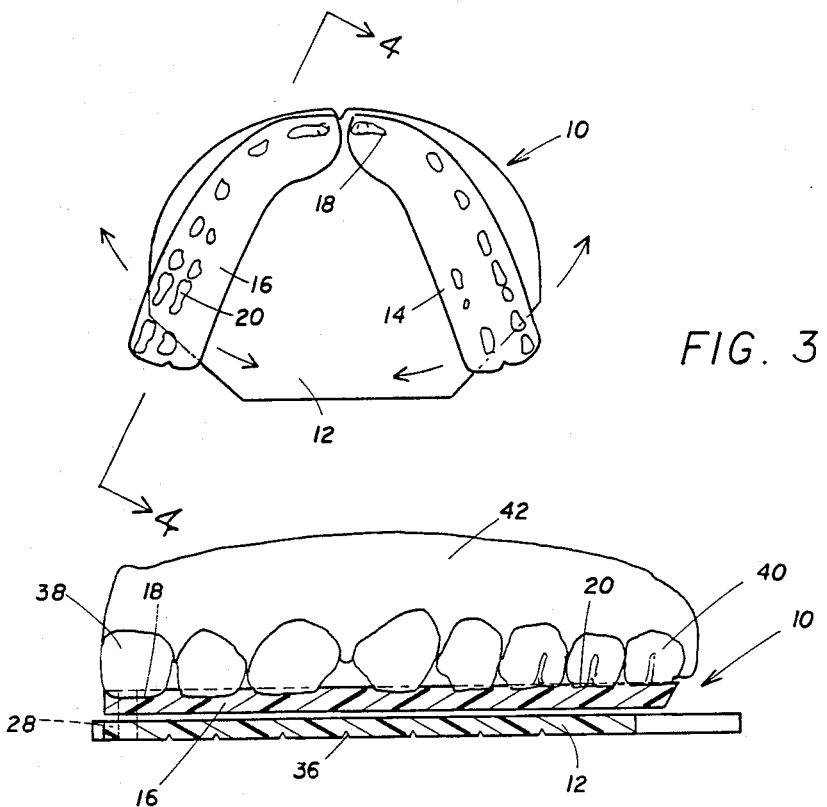
FIG. 3 is a plan view of the template.
FIG. 4 is a section view taken along line 4—4 of FIG. 3.

As shown particularly in FIG. 4, the indentations 18 and 20 are adapted to receive the biting or grinding portions of artificial teeth 38 and 40, and are of progressively shallower depth to follow the "Curve of Spee" along which the biting surfaces are ideally disposed.

In operation, the dental technician selects artificial teeth 38 and 40 to be used and positions them in the indentations or receptacles 18 and 20. The indentations 18 and 20 are formed so that the teeth, when placed, will each be disposed at its desired angle of inclination. Melted wax 44 or the like may be applied to hold each tooth in place on the base plate 42.

Once the upper denture is set up as described, the template 10 may be removed from the lower jaw model 22 and the lower denture set to "mesh" with the upper denture.

While this invention has been described in conjunction with a preferred embodiment thereof, it is obvious that modifications and changes therein may be made by those skilled in the art to which it pertains without departing from the spirit and scope of this invention, as defined by the claims appended hereto.

What is claimed as invention is:

1. A template for setting artificial teeth in a denture comprising:
    a base member;
    a pair of ridge forms, each curved to conform to the curvature of one side of a patient's jaw from front to rear;
    pivot means at the front end of each said ridge form pivotally mounting said ridge form to said base to that said ridge forms may be pivotally adjusted in accordance with the size of the patient's jaw;
    an arch of indentations in the surface of said ridge forms, each said indentation being positioned to receive the biting or grinding portion of a tooth in a desired arrangement of teeth in said jaw; and
    a mark at the rear end of each of said ridge forms to enable one to align said ridge forms with a model of the patient's jaw.

2. The template defined by claim 1 wherein:
    said mark is a notch in the trailing end of said ridge form.

3. The template defined by claim 1 wherein:

said indentations are progressively shallower from front to rear of each of said ridge forms.
4. The template defined by claim 1 including:
a mark at the center front portion of said base member to be aligned with the midpoint of said model.
5. The template defined by claim 1 wherein: said indentations represent the locations of the teeth in the upper jaw of said patient.
6. The template defined by claim 1 including:
means forming surface irregularities on the bottom of said base member to enhance surface gripping.

* * * * *